(12) United States Patent
Trogolo

(10) Patent No.: US 7,598,300 B2
(45) Date of Patent: Oct. 6, 2009

(54) ANTIMICROBIAL COATING FOR EROSIVE ENVIRONMENTS

(75) Inventor: Jeffrey A. Trogolo, Boston, MA (US)

(73) Assignee: Agion Technologies, Wakefield, MA (US)

( * ) Notice: Subject to any disclaimer, the term of this patent is extended or adjusted under 35 U.S.C. 154(b) by 0 days.

(21) Appl. No.: 12/006,139

(22) Filed: Dec. 31, 2007

(65) Prior Publication Data
US 2008/0124369 A1 May 29, 2008

Related U.S. Application Data

(62) Division of application No. 10/875,451, filed on Jun. 24, 2004.

(51) Int. Cl.
*C08K 3/10* (2006.01)
*C08K 3/34* (2006.01)
*C08K 9/10* (2006.01)
*C09D 5/14* (2006.01)

(52) U.S. Cl. ............... 523/122; 523/206; 524/403; 524/408; 524/413; 524/450; 424/409; 427/385.5; 428/323; 428/423.1

(58) Field of Classification Search ............. 428/132.3, 428/423.1, 323; 523/122, 206; 424/409; 427/385.5; 524/403, 408, 413, 450
See application file for complete search history.

(56) References Cited

U.S. PATENT DOCUMENTS

| | | | |
|---|---|---|---|
| 4,775,585 A | 10/1988 | Hagiwara et al. | |
| 4,959,268 A | 9/1990 | Hagiwara et al. | |
| 5,096,958 A | 3/1992 | Meguro et al. | |
| 5,305,827 A | 4/1994 | Steele et al. | |
| 5,376,411 A | 12/1994 | Nishishita | |
| 5,527,854 A | 6/1996 | Matsukawa et al. | |
| 5,556,699 A | 9/1996 | Niira et al. | |
| 5,650,446 A | 7/1997 | Wellinghoff et al. | |
| 6,013,275 A | 1/2000 | Konagaya et al. | |
| 6,123,925 A | 9/2000 | Barry et al. | |
| 6,287,285 B1 | 9/2001 | Michal et al. | |
| 6,436,422 B1 | 8/2002 | Trogolo et al. | |
| 2002/0068093 A1 * | 6/2002 | Trogolo et al. | 424/618 |
| 2003/0118658 A1 | 6/2003 | Trogolo et al. | |
| 2003/0118664 A1 | 6/2003 | Trogolo et al. | |

FOREIGN PATENT DOCUMENTS

| JP | 11222402 | 8/1999 |
|---|---|---|
| JP | 2000028286 | 1/2000 |

* cited by examiner

*Primary Examiner*—Krielliion A Sanders
(74) *Attorney, Agent, or Firm*—IP & L Solutions; Edward K Welch II

(57) ABSTRACT

This invention provides for a curable antimicrobial coating system comprising a base coating composition and a top coat coating composition wherein each contains and antimicrobial agent. The base coat forms a non-hydrophilic polymer layer and the top coat preferably forms a hydrophilic polymer layer or a non-hydrophilic polymer layer which does not preclude the release of the antimicrobial agent. This two-layer coating is especially designed for erosive environments and provides continual antimicrobial activity regardless of the stage of wear or erosion.

23 Claims, 5 Drawing Sheets

ANTIMICROBIAL COATING FOR EROSIVE ENVIRONMENTS

This application is a division of pending U.S. patent application Ser. No. 10/875,451 filed on Jun. 24, 2004.

FIELD OF THE INVENTION

This invention relates to a two-layer coating system wherein each layer contains an antimicrobial agent and wherein the top coat comprises a non-skinning or a hydrophilic polymer coating.

BACKGROUND OF THE INVENTION

A number of inorganic materials have been shown to possess antimicrobial activity. They include metal ions such as silver, copper, zinc, mercury, tin, lead, bismuth, cadmium, chromium and thallium ions. It is theorized that these antimicrobial metal ions exert their effects by disrupting respiration and electron transport systems upon absorption into bacterial or fungal cells. Antimicrobial metal ions of silver, copper, zinc, and gold, in particular, are considered safe for in vivo use. Antimicrobial silver ions are particularly useful for in vivo uses due to the fact that they have the highest ratio of antimicrobial efficacy to human toxicity.

Antimicrobial zeolites can be prepared by replacing all or part of the ion-exchangeable ions in zeolite with antimicrobial metal ions, as described in U.S. Pat. Nos. 4,911,898; 4,911,899; 4,938,955; 4,906,464; and 4,775,585.

Zirconium compounds, such as zirconium phosphates, have also been modified to provide antimicrobial characteristics, as described in U.S. Pat. Nos. 4,025,608 and 4,059,679. J. Antibact. Antifung. Agents Vol. 22, No. 10, pp. 595-601, 1994 and the references therein describe the antimicrobial characteristics of zirconium phosphate ceramics.

Antimicrobial water soluble glasses have been used and are described in U.S. Pat. No. 5,470,585.

Antimicrobial hydroxyapatite powders have been prepared and are described in U.S. Pat. Nos. 5,009,898 and 5,268,174.

U.S. Pat. No. 4,775,585 discloses incorporating metal-zeolite into a polymer to obtain a polymer with bactericidal activity. U.S. Pat. No. 4,923,450 discloses incorporating zeolite in bulk materials for production of medical tubes.

U.S. Pat. No. 6,436,422 discloses an antimicrobial-coated substrate comprising an antimicrobial coating composition coated on a substrate. The antimicrobial coating composition comprises a hydrophilic polymer having antimicrobial ceramic particles dispersed therein.

U.S. Pat. No. 5,238,749 describes a two-layer antimicrobial coating with a top layer using a thermoplastic material selected from the group consisting of nylon 6, nylon 6-6, nylon 11, polyvinylidene fluoride polymer and the family of polyethylene thermoplastic resins, with nylon 11 being preferred. The antimicrobial agent is 5-chloro-2-(2,4-dichlorophenoxy)phenol or polyhexamethylene biguanide hydrochloride. The selection of the organic antimicrobial agent is based on its ability to migrate through the polymer due to the antimicrobial agent's low vapor pressure. However, the use organic antimicrobial agents with low enough vapor pressures oftentimes results in poor surface appearance and limited life due to the ease with which the antimicrobial agent passes through the polymer and blooms to the surface. The tendency is for these organic antimicrobial materials to bloom to the surface continually until the supply or concentration of material is exhausted.

The use of inorganic antimicrobial agents, particularly those whose activity is based on antimicrobial metal ions, can sometimes overcome these problems. However, these antimicrobial agents rely upon moisture or another solvent to dissolve/dissociate and/or transport the active antimicrobial agent. With the ion-exchange type inorganic antimicrobial agents, moisture is needed to carry in the ions to be exchanged and carry out the antimicrobial ions. In polymers such as nylon 11, transport of antimicrobial metal ions can be poor, if existent at all, due the non-hydrophilic nature of the polymer. Specifically, nylon 11 typically manifests a moisture absorption capability of only about 0.2%. This low level of moisture is, at best, marginally sufficient to provide adequate ion exchange and transport through the polymer matrix in which the antimicrobial agent is dispersed. Consequently, such systems have limited antimicrobial efficacy due to poor transport of the metal ions.

One of the problems in the prior art is that coating systems often require a compromise amongst several desirable properties. Formulating a coating with a hydrophilic polymer enables the use of antimicrobial metal ions and gives the desired initial boost of antimicrobial effectiveness. However, these coatings are typically easily abraded in any erosive environment and do not give lasting protection. By choosing non-hydrophilic polymers as the coating matrix, the wear properties can be improved due to the stronger physical performance characteristics and properties, but there are problems with obtaining good antimicrobial activity. Oftentimes these polymer materials skin over the antimicrobial agent, preventing the direct exposure of the antimicrobial agent to the coating surface. This results in the unavailability, for the most part, of that quantity of the antimicrobial agent that lies beneath the surface of the coating into which it is incorporated until the antimicrobial agent is exposed by erosion. Again, due to the low moisture absorption of the non-hydrophilic polymers, migration of the antimicrobial ions can be poor, if existent at all. Thus, the entombed antimicrobial agent is without utility or efficacy. Where the matrix does not completely entomb the antimicrobial particles, oftentimes the use of a larger quantity of antimicrobial agent is required so as to provide a higher concentration at the surface. This, however, is more costly and often imparts deleterious properties. These problems can be exacerbated by surfactants and leveling agents commonly used in coating systems and designed to form a skin at the surface of the coating to control surface finish. This same skin can also form over the antimicrobial agent.

There remains a need to provide an antimicrobial coating in a form that is suitable to impart antimicrobial properties without the accompanying problems of the prior art. More specifically, there remains a need to provide an antimicrobial coating that provides excellent antimicrobial activity upon application of the coating as well as good long-term antimicrobial activity and durability.

SUMMARY OF THE INVENTION

This invention provides for curable antimicrobial coating systems comprising a base coat composition and a top coat composition. The base coat contains an antimicrobial agent and is preferably a highly durable material. A top coat is placed over the base coat. The top coat contains a hydrophilic polymer and an antimicrobial agent. In an alternate embodiment of this invention, the top coat polymer is non hydrophilic and the top coat thickness is, at most, slightly thicker, but is preferably about the same as or less than the average diameter particle size of the antimicrobial agent or the top coat is of such a composition as does not facilitate skinning of the antimicrobial agent. This curable two-layer coating system is useful for erosive environments, i.e., any environment where the coating is gradually worn away due to environmental, cleaning or traffic considerations.

DETAILED DESCRIPTION OF THE DRAWINGS

DETAILED DESCRIPTION OF THE INVENTION

Figure 1:
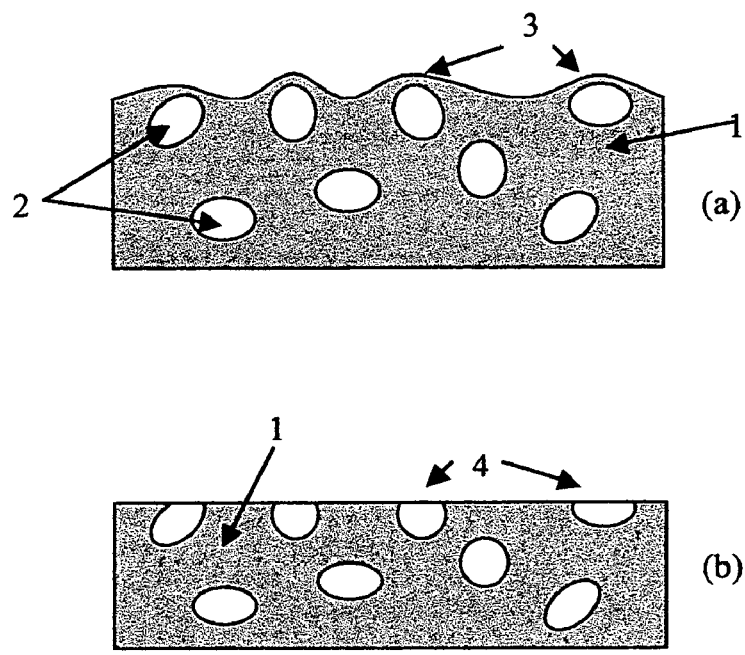
FIG. 1(a) is a schematic cross section of a portion of a base coat having dispersed therein an encapsulated antimicrobial agent following application to a substrate.
FIG. 1(b) is a representation of the same schematic cross-section as in FIG. 1(a) following erosion.

All patent applications, patents, patent publications, and literature references cited in this specification are hereby incorporated by reference in their entirety. In the case of inconsistencies, the present description, including definitions, is intended to control.

This invention provides for a curable antimicrobial coating system useful for erosive environments. Both the curable base coat and the curable top coat contain an antimicrobial agent. When used herein and in the appended claims, the terms "curable", "cure" or "set" refer to the ability or transformation of a liquid or a flowable 100% solids coating composition to a solid, finished coating. Most often reference to cure or cured will be in reference to traditional thermoset or cross-linkable coating composition. However, these terms as well as the term "set" is also used in relation to those coatings that form through solvent evaporation or a combination thereof with cross-linking.

The antimicrobial agent contains a metal or metal ion that can impart antimicrobial activity. Examples of such metal ions include silver, copper, zinc, tin, gold, mercury, lead, iron, cobalt, nickel, manganese, arsenic, antimony, bismuth, barium, cadmium, chromium and thallium ions and combinations thereof. Metal ions of silver, copper, zinc, and gold are preferred because they are considered safe for in vivo use. Silver and/or copper ions are more preferred due to the fact that they have the highest ratios of efficacy to toxicity, i.e., high bio-efficacy (antimicrobial kill) with low environmental/human toxicity: the former for bacterial contaminants and the latter for mold.

In addition to the metal or metal ion that imparts antimicrobial activity, optionally the antimicrobial agent may include or be used in conjunction with discoloration inhibiting agents and/or dopants. Preferred discoloration inhibiting agents include, but are not limited to inorganic discoloration inhibitors such as those of various ammonium salts. Dopants, which are particularly of use with the ion-exchange type antimicrobial agents, aid in the transport of the antimicrobial metal ion. These dopants provide a ready source of cations which exchange with and replace the antimicrobial silver metal ions in the ion-exchange ceramic particles, thereby facilitating release and transport of the silver ion. Preferred dopants include, but are not limited to inorganic salts of sodium such as sodium nitrate. For example, if sodium nitrate is used with a silver containing ion-exchange type antimicrobial agent, the sodium nitrate dissociates providing sodium ions which exchange with the antimicrobial silver ions, thereby releasing the silver ion for transport to the surface. In this example, the sodium nitrate expedites the release of the silver from the antimicrobial agent.

The antimicrobial agent can be in the form of a simple salt of the antimicrobial metal such as the oxide, sulfide, chloride, bromide, carbonate, nitrate, phosphate, dihydrogen phosphate, sulfate, oxalate, acetate, benzoate, thiosulfate and the like. Specific examples include silver nitrate, cupric oxide, zinc acetate and zinc oxide.

Alternatively, the antimicrobial agent may be in the form of a water soluble glass containing the antimicrobial agent or compound. Suitable antimicrobial water soluble glasses include those disclose in U.S. Pat. No. 5,470,585. By suitable adjustment of the glass composition, the dissolution rates in water can be controlled.

Preferably, the antimicrobial agent will be in the form of an ion-exchange type ceramic particle wherein antimicrobial metal ions have been exchanged (replaced) for other non-antimicrobially effective ions in the ceramic particles or a combination of the foregoing with an antimicrobial metal salt. Antimicrobial ceramic particles include, but are not limited to zeolites, hydroxyapatite, zirconium phosphates and other ion-exchange ceramics. Hydroxyapatite particles containing antimicrobial metals are described, e.g., in U.S. Pat. No. 5,009,898. Zirconium phosphates containing antimicrobial metals are described, e.g., in U.S. Pat. Nos. 5,296,238; 5,441,717 and 5,405,644. More preferably, the antimicrobial agent is an antimicrobial zeolite containing ion-exchanged antimicrobial metal ions.

Generally speaking, the antimicrobial zeolite used in the preferred embodiment of the present invention a prepared by an ion-exchange reaction in which non-antimicrobial ions present in the zeolite, such as sodium ions, calcium ions, potassium ions and iron ions, are partially or wholly replaced with antimicrobial metal ions. Optionally, other ions may also be exchanged for better efficacy and/or color stability, including ammonium ions. Such ions may co-exist in the antimicrobial zeolite particle since they do not prevent the bactericidal effect. Examples of antimicrobial metal ions include, but are not limited to, ions of silver, copper, zinc, gold, mercury, tin, lead, bismuth, cadmium, chromium and thallium. Preferably, the antimicrobial metal ions are silver, copper or zinc ions or combinations thereof, and most preferably silver is employed alone or together with one or both of the others. Thus, one is able to tailor the antimicrobial agent by selection of specific metal ions and combinations thereof to be incorporated into the zeolite or other carrier particle for particular end-use applications.

The antimicrobial metal ion is present in the range of from about 0.1 to about 25 wt % of the zeolite based upon 100% total weight of zeolite. Preferably, the antimicrobial metal ion is present in the range of from about 0.3 to about 20 wt % of the zeolite based upon 100% total weight of zeolite. Most preferably, the antimicrobial metal ion is present in the range of from about 2 to about 10 wt % of the zeolite based upon 100% total weight of zeolite. In one embodiment, the zeolite contains from about 0.1 to about 15 wt % of silver ions and from about 0.1 to about 15 wt % of copper and/or zinc ions. Although ammonium ion may be contained in the zeolite at a concentration as high as about 20 wt % of the zeolite, it is desirable to limit the content of ammonium ions to from about 0.1 to about 2.5 wt % of the zeolite, more preferably from about 0.25 to about 2.0 wt %, and most preferably, from 0.5 to about 1.5 wt %.

Antimicrobial zeolites, including the antimicrobial zeolites disclosed in U.S. Pat. Nos. 4,911,898; 4,911,899 and 4,938,958, are well known and may be prepared for use in the present invention using known methods.

Either natural zeolites or synthetic zeolites may be used to prepare the antimicrobial zeolites used in the present invention. "Zeolite" is an aluminosilicate having a three dimensional skeletal structure that is represented by the formula: $XM_2/nO$—$Al_2O_3$—$YSiO_2$-$ZH_2O$. M represents an ion-exchangeable ion, generally a monovalent or divalent metal ion; n represents the atomic valency of the (metal) ion; X and Y represent coefficients of metal oxide and silica, respectively; and Z represents the number of water of crystallization. Examples of such zeolites include A-type zeolites, X-type zeolites, Y-type zeolites, T-type zeolites, high-silica zeolites, sodalite, mordenite, analcite, clinoptilolite, chabazite and erionite. The present invention is not restricted to use of these specific zeolites.

The ion-exchange capacities of these zeolites are as follows: A-type zeolite=7 meq/g; X-type zeolite=6.4 meq/g; Y-type zeolite=5 meq/g; T-type zeolite=3.4 meq/g; sodalite=11.5 meq/g; mordenite=2.6 meq/g; analcite=5 meq/g; clinoptilolite=2.6 meq/g; chabazite=5 meq/g; and erionite=3.8 meq/g. These ion-exchange capacities are sufficient for the zeolites to undergo ion-exchange with ammonium and antimicrobial metal ions.

The specific surface area of preferred zeolite particles is preferably at least 150 m$^2$/g (anhydrous zeolite as standard) and the $SiO_2/Al_2O_3$ mole ratio in the zeolite composition is preferably less than 14 and more preferably less than 11.

The antimicrobial metal ions used in the antimicrobial zeolites should be retained in and on the zeolite particles through an ion-exchange reaction. Antimicrobial zeolites in which the antimicrobial metal ions are solely or predominately adsorbed or attached without an ion-exchange reaction typically exhibit an overall decreased bactericidal effect and their antimicrobial effect is not long lasting. Nevertheless, it can be advantageous for imparting quick antimicrobial action to maintain a sufficient amount of surface adsorbed metal ion in addition to the ion-exchanged metal ion.

The antimicrobial zeolites, as well as other antimicrobial ceramic particles, may also contain a discoloration agent. Preferably, the discoloration agent is biocompatible. Preferred discoloration agents include, but are not limited to, inorganic discoloration inhibitors such as ammonium. More preferably, the inorganic discoloration inhibitor is an ion-exchanged ammonium ion in the zeolite.

A preferred antimicrobial zeolite for use in the invention is type A zeolite containing ion-exchanged silver, zinc, and/or copper ions in combination with ammonium ions; more preferably combinations of the silver and copper ions with the ammonium ions or just silver ions and ammonium ions. A family of such zeolite antimicrobial agents is distributed by AgION Technologies, Inc. (Wakefield, Mass., USA) under AgION trademark. One grade, AW-10N, consists of 0.6% by weight of silver ion-exchanged in Type A zeolite particles having a mean average diameter of about 3μ. Another grade, AJ-10N, consists of about 2% by weight of silver ion-exchanged in Type A zeolite particles having a mean average diameter of about 3μ. Yet another grade, AW-80, contains 0.6% by weight of silver ion-exchanged in Type A zeolite particles having a mean average diameter of about 2μ. Another grade, AJ-80N, consists of about 2% by weight of silver ion-exchanged in Type A zeolite particles having a mean average diameter of about 1μ. Each of the above also contain about 14% by weight zinc in combination with between about 0.5% and 2.5% by weight of ion-exchanged ammonium, the latter typically present as a discoloration inhibiting agent.

The antimicrobial agent to be used in the practice of the present invention can be encapsulated as described in United States Published Patent Application No. US2003-0118664 A1 (U.S. Ser. No. 10/032,372 filed Dec. 21, 2001 by Trogolo et al.), which is incorporated herein by reference. Although the encapsulated antimicrobial agent may be used in either or both the top coat and the base coat, it is preferably used in the base coat. Generally speaking, the encapsulated antimicrobial agent is in the form of microcapsules or particles that comprise either a single particle or, most preferably, a plurality (several to several hundred or more) of particles of the antimicrobial agent encapsulated within a hydrophilic polymer. The encapsulated antimicrobial agent may be of many shapes and may deform somewhat during processing of the coating. Generally, the encapsulated antimicrobial agent will be in the form of particles having a low aspect ratio, for example, on the order of from 1 to about 4, preferably from 1 to about 2, most preferably from 1 to about 1.5. However, it is also contemplated that microcapsules may be of a high aspect ratio as taught in United States Published Patent Application No. US2003-0118658 A1 (U.S. Ser. No. 10/032,370 filed Dec. 21, 2001 by Trogolo et al), also incorporated herein by reference. These high aspect ratio microcapsules are typically in the shape of flakes and fibers whose aspect ratio is up to 100 or more, but typically is less than about 30.

The hydrophilic polymers suitable for use in encapsulating the antimicrobial agent are those that can absorb sufficient water to enable the encapsulated particle to exhibit good antimicrobial behavior, i.e., to allow for the migration and release of the antimicrobial active agent. These polymers are characterized as having water absorption at equilibrium of at least about 2% by weight, preferably at least about 5% by weight, more preferably at least about 20% by weight, as measured by ASTM D570. Especially suitable hydrophilic polymers include those having water contents at equilibrium of from about 50 and to about 150% by weight.

The encapsulating hydrophilic polymers, hereinafter oftentimes referred to as the encapsulant, are typically comprised of substantial quantities of monomers having polar groups associated with them, such that the overall polymeric composition is rendered hydrophilic. The polar groups can be incorporated into the polymer main chain as in for example polyesters, polyurethanes, polyethers or polyamides. Optionally the polar groups can be pendant to the main chain as in for example, polyvinyl alcohol, polyacrylic acids or as in ionomers such as Surlyn®. Surlyn® is available from Dupont and is the random copolymer poly(ethylene-co-methacrylic acid) wherein some or all of the methacrylic acid units are neutralized with a suitable cation, commonly $Na^+$ or $Zn^{+2}$. While not being limited by way of theory, it is believed that the inclusion of polar groups allows water to more readily permeate the polymer and consequently, to allow slow transport of the metal ion through the encapsulating polymer layer. Such encapsulants may be thermoplastic or they may be thermoset or cross-linked.

A number of specific hydrophilic polymers suitable for use as the encapsulant include, for example, (poly)hydroxyethyl methacrylate, (poly)hydroxypropyl methacrylate, (poly) glycerol methacrylate, copolymers of hydroxyethyl methacrylate and/or methacrylic acid, polyacrylamide, hyaluronan, polysaccharides, polylactic acid, copolymers of lactic acid, (poly)vinyl pyrrolidone, polyamides such as Nylon 6,6 or Nylon 4,6 or Nylon 6,12, cellulosics, polyureas, polyurethanes and certain polyesters containing a high percentage (at least about 10% by weight, preferably at least about 25% by weight or more) of polyalkylene oxide.

The hydrophilic polymer may be a copolymer containing at least a substantial amount of at least one or more of the above-mentioned hydrophilic monomers, including, for example, styrene/methacrylic acid/hydroxyethyl methacrylate copolymers, styrene/methacrylic acid/hydroxypropyl methacrylate copolymers, methylmethacrylate/-methacrylic acid copolymers, ethyl methacrylate/styrene/methacrylic acid copolymers and ethyl methacrylate/methyl methacrylate/styrene/methacrylic acid copolymers, copolymers based upon the cellulosics, and copolymers which utilize vinylpyrrolidone monomers, among numerous others, especially copolymers of n-vinylpyrrolidone and polymethylmethacrylate.

Other encapsulants include polyvinyl acetate, polyvinyl alcohol, and copolymers of polyvinyl alcohol and polyvinylacetate, polyvinylchloride, copolymers of polyvinylacetate and polyvinylchloride and hydroxyl-modified vinyl chloride/vinyl acetate copolymers.

Polyurethanes containing a high percentage (at least about 10% by weight, preferably at least about 25% by weight or more) of polyalkylene oxide are especially useful in this invention.

Preferably the encapsulating hydrophilic polymer is chosen from polyhydroxyethyl methacrylate, polyacrylamide, polyvinylpyrrolidinone, polyurea, polysaccharides, polylactic acid and polyurethane and copolymers thereof. More preferably, the hydrophilic polymer is hydrophilic polyurethane, such as the TECOPHILIC® polyurethane sold by Thermedics of Woburn, Mass. or a lightly cross-linked polymer based on n-vinylpyrrolidone and methylmethacrylate sold under the trade designation AEP Polymers by IH Polymeric Products Limited of Kent, England.

While the encapsulated antimicrobial agent may be in the form of individually encapsulated antimicrobial particles having a coating thickness of up to 15μ, more typically and preferably, the they are in the form of larger microcapsules containing multiple antimicrobial particles, especially of the ion-exchange type. These microcapsules may have a mean average diameter of up to and over 2000μ, but not likely over 3000μ. Generally the microcapsules will have a mean average diameter of from about 15μ to about 1000μ, preferably from about 50μ to about 300μ, most preferably from about 90μ to about 200μ. Of course smaller or larger microcapsules can be used. However, the smaller the microcapsule the more closely one approaches a system of individually encapsulated particles. Similarly, the larger the particles, the more potential there is for a deleterious effect on the physical properties of the polymer matrix and the greater the distance between particles at the surface, in the case of equivalent weights of larger versus small particle size microcapsules. Of course, microcapsule size and shape is somewhat dependent upon the size and shape of the antimicrobial particles to be incorporated therein as well as the process by which the microcapsules are made.

The encapsulated antimicrobial agents are especially useful in the base coat materials since they serve as a reservoir of antimicrobial agent wherein all of the antimicrobial agent within the encapsulant particle is available since the hydrophilic nature of the encapsulating polymer allows for ready transport of the antimicrobial ions through the encapsulant particle and, thus, to the surface of the coating which intersects with that particle. In the case of the use of the encapsulated materials in a top coat that is also hydrophilic, the encapsulating material, if of lower hydrophilicity, will serve to slow the release of the antimicrobial ions from the coating since the hydrophilicity of the encapsulating polymer, as opposed to the top coat matrix, will determine the rate at which transport occurs. Encapsulation is also important since it increases the effective size of the antimicrobial agent, thus, ensuring a greater likelihood that as the coating erodes, more particles will intersect the surface and be able to release the antimicrobial active agent or ion. When the encapsulated particles are employed, it is understood that the encapsulating polymer is not compatible with the matrix of the top coat and/or base coat in which it is incorporated: the lack of compatibility being evidenced by the presence of these encapsulant particles as a discrete phase in the coating matrix. The encapsulating polymer may, however, be compatible from the perspective of having good adhesion or affinity for the coating matrix so long as the discrete phase is maintained.

The two-layer coating has a bottom base coat and a top coat. The base coat is polymer based. The choice of the base coat polymer depends upon the application. Typically the polymer is chosen to maximize properties such as adhesion, wear, and appearance.

The polymer chosen for the base coat can be thermoplastic or thermoset (i.e., cross-linkable). Suitable thermoplastic polymers include, but are not limited to, polypropylene, polyethylene, polystyrene, ABS, SAN, polybutylene terephthalate, polyethylene terephthalate, nylon 6, nylon 6,6, nylon 4,6, nylon 12, polyvinylchloride, polyurethanes, silicone polymers, polycarbonates, polyphenylene ethers, polyamides, polyethylene vinyl acetate, polyethylene ethyl acrylate, polylactic acid, polysaccharides, polytetrafluoroethylene, polyimides, polysulfones, and a variety of other polymers and copolymers. Preferably, the polymer chosen for the base coat is a thermoset or cross-linkable polymer. Suitable thermoset/cross-linkable polymers include, but are not limited to, phenolic resins, urea resins, epoxy resins, polyesters, epoxy polyesters, acrylics, acrylic and methacrylic esters, polyurethanes and a variety of other polymers and copolymers. Epoxy resins are preferred due to their excellent adhesion to a variety of substrates and durability.

The base coat will generally contain from about 1% to about 30%, preferably from about 5% to about 20% and most preferably from about 5% to about 10%, by weight of the antimicrobial agent based on the total weight of the cured base coat, i.e., the solids. The foregoing ranges also hold true for the encapsulated antimicrobial agents except that the weight percent of the antimicrobial agent is based on the weight of just the antimicrobial agent exclusive of the encapsulation material.

The base coat formulation can contain other additives such as UV or thermal stabilizers, adhesion promoters, dyes or pigments, leveling agents, fillers and solvents. The formulation will depend upon the end use application and the choice of the polymer. The antimicrobial agent is mixed with the base coat formulation prior to application. When the base coat formulation contains several parts, such as in a two-part epoxy base coat, the antimicrobial agent can be mixed with one part prior to mixing the remaining parts or it can be mixed during or after the mixing of the individual parts.

As noted previously, the antimicrobial agent to be used in the base coat is preferably one that is encapsulated with a hydrophilic polymer and most preferably comprises many particles of the antimicrobial agent in each microcapsule or particle of the encapsulated material. When the antimicrobial agent is encapsulated with a hydrophilic polymer, the combination of base coat formulation and hydrophilic polymer should be chosen such that the hydrophilic polymer encapsulating the antimicrobial agent does not dissolve in the base coat formulation. Additionally, it is preferred that the hydrophilic polymer encapsulant and the base coat matrix have good adhesion of one to the other. Otherwise, as particles are exposed, there is the risk that the particles will be easily dislodged from the coating surface reducing the antimicrobial efficacy of the overall coating.

In the preferred embodiment of this invention, the top coat formulation contains a hydrophilic polymer and an antimicrobial agent. By hydrophilic polymer, we mean a polymer that can absorb sufficient water to enable the antimicrobial agent to exhibit good antimicrobial behavior, i.e., to allow for the migration and release of the antimicrobial active agent. The polymer will be characterized by having water absorption at equilibrium of at least about 2% by weight measured by ASTM D570. Preferably, the polymer will have water absorption at equilibrium of at least about 5% by weight. More preferably, the polymer will have water absorption at equilibrium of at least about 20% by weight. Especially suitable hydrophilic polymers include those having water absorption capabilities at equilibrium of from about 50% and to about 150% by weight.

Hydrophilic polymeric compositions for use as the top coat in the present invention include polymers, which are comprised of substantial quantities of monomers having polar groups associated with them, such that the overall polymeric composition is rendered hydrophilic. The polar groups can be incorporated into the polymer main chain as in for example polyesters, polyurethanes, polyethers or polyamides. Optionally the polar groups can be pendant to the main chain as in for example, polyvinyl alcohol, polyacrylic acids or as in ionomers such as Surlyn®. Surlyn® ionomer resins are available from Dupont and is the random copolymer poly(ethylene-co-methacrylic acid) wherein some or all of the methacrylic acid units are neutralized with a suitable cation, commonly $Na^+$ or $Zn^{+2}$. While not being limited by way of theory, it is believed that the inclusion of polar groups allows water to more readily permeate the polymer and consequently, to allow transport of the metal ion through the top coat polymer layer.

As another option, the top coat can be made hydrophilic by blending a hydrophilic polymer with a non-hydrophilic polymer and/or cross-linkable coating polymer precursor. A preferred blend is made by using a supporting polymer comprising a plurality of functional moieties capable of undergoing crosslinking reactions, said supporting polymer soluble in or emulsified in an aqueous based medium; and a hydrophilic polymer, said hydrophilic polymer associated with the supporting polymer as described in U.S. Pat. No. 6,238,799. The ratio of the hydrophilic to non-hydrophilic and/or cross-linkable polymer depends on the hydrophilicity of the hydrophilic polymer and the desired hydrophilicity of the resultant blend. Generally speaking, the amount should be such that the resultant blend will have the ability to absorb at least 2% by weight, preferably at least 5% by weight, most preferably at least 20% by weight of water at equilibrium as measured by ASTM D570. Those skilled in the art will readily be able to determine the proper ratio of components based on models and/or simple experimentation.

A number of hydrophilic polymers may be used in the present invention and include, for example, polyacrylates and polymethacrylates including (poly)hydroxyethyl methacrylate, (poly)hydroxypropyl methacrylate, (poly)glycerol methacrylate, copolymers of hydroxyethyl methacrylate and methacrylic acid; polyacrylamides; polymethacrylamides; hyaluronan; polysaccharides; polylactic acid; copolymers of lactic acid; (poly)vinyl pyrrolidone; polyamides such as Nylon 6,6, Nylon 4,6 and Nylon 6,12; cellulosics; polyureas; polyurethanes and certain polyesters containing a high percentage (at least about 10% by weight, preferably at least about 25% by weight or more) of polyalkylene oxide.

The hydrophilic polymer may be a copolymer containing at least a substantial amount of at least one or more of the above-mentioned hydrophilic monomers, including, for example, styrene/methacrylic acid/hydroxyethyl methacrylate copolymers, styrene/methacrylic acid/hydroxypropyl methacrylate copolymers, methyl methacrylate/-methacrylic acid copolymers, ethyl methacrylate/styrene/methacrylic acid copolymers and ethyl methacrylate/methyl methacrylate/styrene/methacrylic acid copolymers, copolymers based upon the cellulosics, and copolymers which utilize vinyl pyrrolidone monomers, among numerous others.

Other hydrophilic polymers that may be used in the present invention include polyvinyl acetate, polyvinyl alcohol, and copolymers of polyvinyl alcohol and polyvinylacetate, polyvinylchloride, copolymers of polyvinyl acetate and polyvinylchloride and hydroxyl-modified vinyl chloride/vinyl acetate copolymers.

Polyurethanes containing a high percentage (at least about 10% by weight, preferably at least about 25% by weight or more) of polyalkylene oxide are especially useful in this invention.

Preferably the hydrophilic polymer is chosen from polyacrylates and poly(meth)acrylates (especially polyhydroxyethyl methacrylate), polyacrylamide, polyvinylpyrrolidinone, polyurea, polysaccharides, polylactic acid and polyurethane. More preferably, the hydrophilic polymer is hydrophilic polyurethane, such as the TECOPHILIC® polyurethane sold by Thermedics of Woburn, Mass., the AEP Polymers from 1H Polymeric Products of Kent, England, or an (meth)acrylic ester based coating from Surface Solutions Laboratories, Inc. of Carlisle, Mass.

In yet another embodiment of the present invention, the top coat may be a non-hydrophilic material provided that it does not skin over so that the antimicrobial particles are present at the surface and capable of immediately releasing the antimicrobial agent without abrading the surface thereof. As with the hydrophilic coatings, these top coat materials are generally less durable than the underlying base coat material or, in any event, are unsuitable for use as the base coat itself due to appearance or physical properties. These non-hydrophilic top coats may be thermoset (cross-linkable) or thermoplastic and may comprise non-hydrophilic species of the aforementioned hydrophilic polymers. Such non-hydrophilic top coat coating compositions may comprise, for example, an epoxy coating composition.

The top coat compositions will generally contain from about 1% to about 30%, preferably from about 5% to about 20% and most preferably from about 5% to about 10%, by weight of the antimicrobial agent based on the total weight of the cured top coat, i.e., the solids. The foregoing ranges also hold true for the encapsulated antimicrobial agents except that the weight percent of the antimicrobial agent is based on the weight of just the antimicrobial agent exclusive of the encapsulation material.

The top coat formulation can contain other additives such as UV or thermal stabilizers, adhesion promoters, dyes or pigments, leveling agents, fillers and solvents. The formulation will depend upon the end use application and the choice of the polymer. The antimicrobial agent is mixed with the top coat formulation prior to application. Preferably the top coat antimicrobial agent is antimicrobial zeolite.

In addition, both or either of the top coat and the base coat may contain other known antimicrobial additives as well. Such additional additives may be organic or inorganic. Preferred additive antimicrobial agents include antimicrobial quarternary ammonium, phosphonium and/or sulfonium salts and compounds, including those disclosed in Konagaya et. al., U.S. Pat. No. 6,013,275 which is incorporated herein by reference. Additionally, especially where the coatings of the present invention are to be used in environments where fungus is a concern, it is particularly desirable to employ strong antifungal agents, especially the various copper containing antifungal agents including copper quinolinolate. Such additive antimicrobial and antifungal agents are known to those skilled in the art and would be added in their traditional amounts, though lesser amounts could also be used since the primary antimicrobial agents first mentioned above are also present.

The top coat formulation is applied after the base coat has set. The choice of the method will depend upon the application. Both the base coat and top coat can be applied by any of several methods known in the art. Suitable methods include spraying, brushing, rolling, printing, dipping and mold coating.

The selection of the top coat and base coat formulations to be used in any single application should be such that each layer is compatible with the other. The key aspect of compatibility, in this respect, is the adhesion between the layers. If there is insufficient peel strength or adhesive strength between the layers, the top coat may slough off prematurely, before antimicrobial agent in the base coat is exposed. Those skilled in the art will readily recognize, based on the compositions of each, whether compatibility is or will be an issue. For example, typically one would not place an oil-based top coat on a water-based latex base coat. Alternatively, one could prepare simple test pieces with the intended combination of top coat and base coat and evaluate the integrity of the bond between the two coatings.

Generally speaking, the inventive concept of the present invention lies in the use of an antimicrobial top coat to provide immediate ion release capabilities to the coated substrate and a durable antimicrobial base coat to provide long-lived antimicrobial capabilities. As the surface of the newly coated substrate is subjected to erosive conditions, the top coat wears away, exposing the base coat which also wears away exposing the antimicrobial agent that was otherwise skinned over in the formation of the base coat itself. Although the base coat is more durable than the top coat, the thin skin of the base coat overlaying the antimicrobial particles at the surface of the base coat readily wears away, concurrent with the top coat, to expose the underlying antimicrobial agent. Furthermore, since neither the rate of erosion nor the surface layer thickness of the top coat is likely to be consistent across the whole of the coated surface area, this invention ensures the availability of antimicrobial agent across the full surface area. Therefore, regardless of the rate or degree of erosion, silver release will occur.

Figure 2:
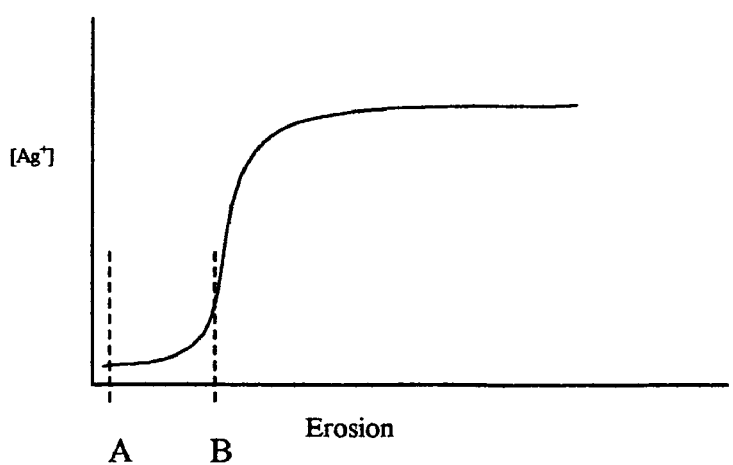
FIG. 2 is a graphic representation of the ion-release characteristics of the base coat over time: time being represented by erosion.

FIG. 1(a) shows a schematic cross-section of a one-layered coating composition (1) containing encapsulated antimicrobial particles (2) dispersed in the coating composition wherein a skin of the coating composition has formed over the particles near the surface (3). FIG. 1(b) shows this same cross-section at a point later in time whereby the upper surface of the coating has worn away exposing the antimicrobial particles (4). The graph in FIG. 2 shows the typical ion release characteristics of such a construction having a high erosion rate under proper release conditions. Initially, there is insignificant, if any, ion release (Point A). As the coating is eroded and the encapsulated particles begin to be exposed, a slow increase in the rate of release of ions occurs (as seen in the transition from Point A to Point B). As erosion continues, more and more particles are exposed until sufficient particles are exposed to provide an efficacious release of antimicrobial ions (Point B). Once the whole, or substantially the whole, of the surface area is eroded, the maximum number of particles is exposed and a relatively constant ion release is attained. The exact plot of the ion release in FIG. 2 will vary widely depending upon the concentration of antimicrobial particles in the coating, the release conditions, and the wear rate. Indeed, rather than the straight line plot as seen in FIG. 2, the plot may be wavy to reflect a slow wear rate and ion depletion before new particles are exposed. Similarly, as one wears through the entire thickness of the coating, ion release will drop off altogether.

Figure 3:
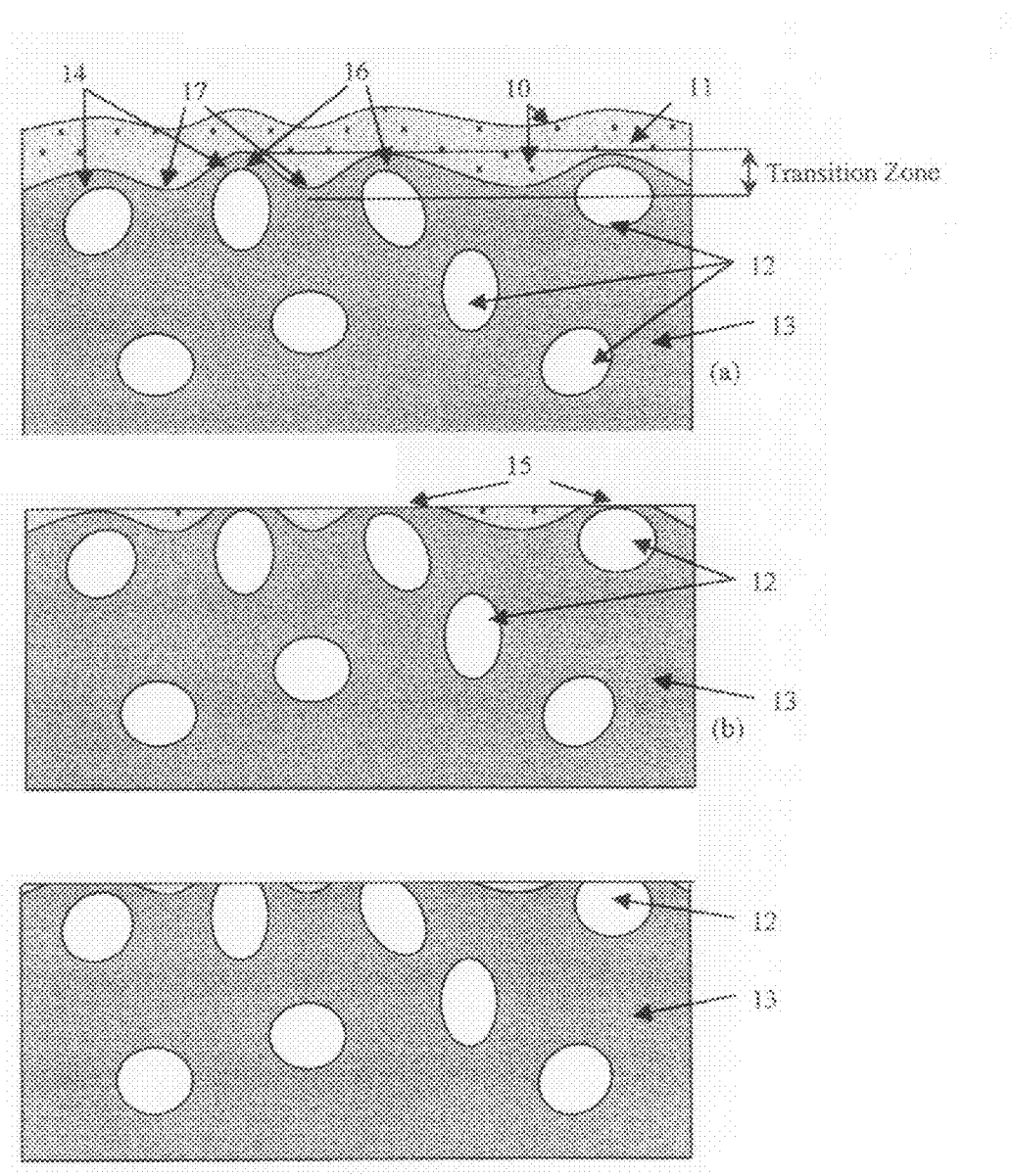
FIG. 3(a) is a schematic cross section of a portion of a two-layer erosive coating according to the practice of the present invention following application to a substrate.
FIG. 3(b) is a representation of the same schematic cross-section as in FIG. 3(a) at the point where the encapsulated antimicrobial in the base coat is exposed.
FIG. 3(c) is a representation of the same schematic cross-section as in FIG. 3(a) at the point where substantially all of the top coat is eroded.

FIG. 3 shows a schematic cross-section of the two-layered coating structure according to the present invention. FIG. 3(a) shows the newly deposited two-layer coating wherein silver is initially released from the antimicrobial particles (10) dispersed in the hydrophilic top coat (11). The encapsulated antimicrobial agent (12) in the base coat (13) remains unavailable due to the skin (14) of base coat intermediate the encapsulated agent and the hydrophilic top coat. As more and more of the top coat is eroded, FIG. 3(b), the base coat (13) becomes exposed (15). This erosion also wears away the skin and begins to expose the encapsulated antimicrobial agent. Most often the exposure of the base coat is uneven due to irregular erosion or wear combined with a non-planar coating topography. Because the top coat is typically, much softer and, thus, less wear resistant than the base coat, erosion of the top coat slows as more and more base coat is exposed. In essence, the peaks of the base coat (16) protect the valleys of the top coat (17). Eventually, as depicted in FIG. 3(c), all or essentially all of the top coat erodes away and the remaining base coat provides continued release from the encapsulated particles (12).

Figure 4:
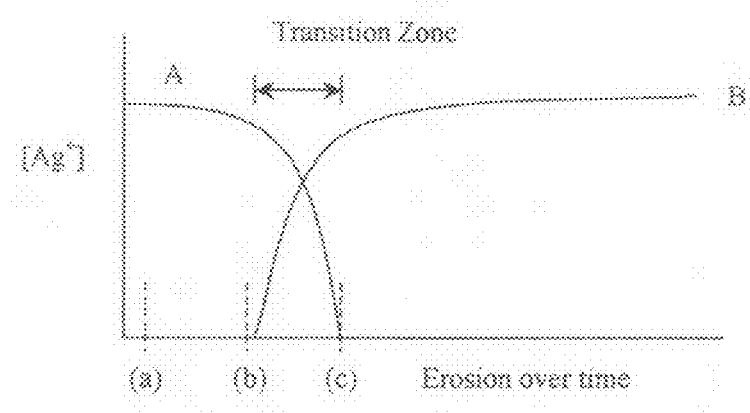
FIG. 4 is a graphic representation of the ion-release characteristics of the two-layered erosive coating over time: time being represented by erosion.

The graph in FIG. 4 depicts the ion release characteristics of a coating system according to the practice of the present invention under proper release conditions, with points (a), (b) and (c) corresponding to FIGS. 3(a), 3(b) and 3(c) respectively. Plot A, representing the release characteristics of the top coat, shows immediate and significant release of silver ions from the newly deposited coating as shown in FIG. 3(a). As the top coat wears away, less and less antimicrobial agent remains and there is a decrease in the amount of silver ion released from the top coat. However, as the base coat is exposed and the skin (14) worn away the encapsulated antimicrobial agent (12) is exposed (FIG. 3(b)). Concurrently, there is a slow, gradual increase in silver ion release from the base coat, as shown by plot B of FIG. 4. Eventually all of the top coat is eroded away leaving only the base coat (FIG. 3(c)), such that only the antimicrobial agent within the base coat contributes to the ion release. It is understood that the depiction in FIG. 4 is for illustrative purposes. The actual rate of ion release and, thus, the ion concentration, will vary depending upon the amount of antimicrobial agent included in each layer, the form of the antimicrobial, and the composition and wear properties of each coating layer, and other factors. Thus, the actual concentration of the ion release from the base coat may be greater, the same as or less than that of the top coat. Similarly, the transition zone (17 in FIG. 4) could be longer or shorter depending upon the wear characteristics of each layer. Additionally, since the wear rate of the top coat is most likely much greater than the wear rate of the base coat, the transition zone depicted by points B and C on FIG. 4, is likely to be much broader with the plots more gentle and somewhat of a half-bell shape as opposed to the sharp curves shown.

By comparing the graphs of FIGS. 2 and 4, one can clearly see that the delayed onset of silver release from the base coat is accommodated for by the release profile from the top coat. The resulting product maintains ion release throughout the erosive life of the coating system.

Reference herein to proper release conditions means that (1) in the case of metal salts and soluble glass based antimicrobial agents, there is sufficient surface moisture to dissociate/dissolve the salt or glass and (2) in the case of ion-exchange antimicrobial agents, there is sufficient moisture and exchangeable cations to enable ion-exchange and, thus, release of the antimicrobial metal ions. When no moisture is present, no ions are released; thus, the particles serve as a reservoir for the antimicrobial agent until the needed. By the same token, antimicrobial release is not needed unless and until moisture is present since bacteria and mold cannot grow in the absence of moisture. The ion-exchange type antimicrobial agents and the soluble glass antimicrobial agents are especially preferred due to the large reservoir of antimicrobial metal ions contained in each and because of the release rate limitations resulting from the solubility parameter of the glass and the ion-exchange rate capability of the ion-exchange particles that carries the ions.

Though the embodiment discussed above depicts a system wherein the antimicrobial agent is in particle form in the top coat and encapsulated form in the base coat, it is understood that encapsulated or non-encapsulated forms of the antimicrobial agent may be used in both coating layers. Generally, one would not need to use the encapsulated form in the top coat unless the hydrophilic nature of the top coat allowed too fast or too slow an ion release and an encapsulant having a lower or higher degree of hydrophilicity were used to slow or increase the release of the antimicrobial metal ions from the top coat, respectively. Similarly, though it is not necessary to use the encapsulated form in the base coat, doing so provides a large reservoir of antimicrobial agent that is readily available once the encapsulated particle is exposed. Although not depicted in the drawings, the encapsulated particles generally comprise a large number of individual antimicrobial particles dispersed in the encapsulating hydrophilic polymer.

The selection and thickness of the coatings depends upon the application requirements and limitation. The thickness and composition of the base coat system can vary widely and is chosen as needed for the application design. A high wear environment may require at thicker coating, especially one of good durability and/or wear resistance. The thickness of the base coat may also be a function of life of the substrate to which it is applied or, if the coating is periodically refinished or removed and replaced, the intended life of the coating itself. Generally, the thickness is the same as would be used for such coating compositions in the absence of the antimicrobial agent. Since, in practice, the antimicrobial agent may be added to commercially available coating compositions, the thickness and rate of application is as recommended by the manufacturer of the same.

Similarly, the thickness and composition of the top coat system is chosen as needed for the application design top coat system, keeping in mind, however, that the thickness is not so critical as for the base coat. Instead, the top coat is preferably applied so as to obtain sufficient thickness such that any surface irregularities or defects in the base coat are covered. Alternatively, where the top coat also serves as a pre-applied protective layer to the underlying base coat for substrates that are coated prior to installation in their intended end-use application the coating thickness may be considerably greater to ensure that the base coat is not prematurely exposed prior to installation of the substrate. For example, many finished, coated metal parts have a release film applied to their surface to protect them during storage and shipment. The release film is peeled off the part when put in use. In accordance with the present invention, a thicker top coat could be applied for the same purpose as the film. Costs are another factor in considering top coat thickness and composition. Typically, the top coat formulation is more expensive than the base coat. For this reason, the thickness of the top coat is preferably no greater than that required by the application needs. Again, since, in practice, the antimicrobial agent may be added to commercially available coating compositions, the thickness and rate of application may be as recommended by the manufacturer of the same; however, again, since the top coat is not the performance coating, thinner layers are equally suitable.

In yet another alternate embodiment of this invention, the top coat polymer is a skin forming non-hydrophilic composition provided that the thickness of the cured top coat is, at most, slightly thicker than, but preferably the same as or less than, the average diameter particle size of the antimicrobial agent. In this embodiment, the thickness of the top coat is generally and preferably less than about 20 microns and more preferably less than about 3 microns. The choice of the antimicrobial to be used would be determined by the final top coat thickness. For instance, for a top coat thickness of 3 microns, about a 3 micron or larger average diameter particle size antimicrobial agent would be used. On the other hand, if a microencapsulated antimicrobial agent is used in the top coat, for example one having a particle size of 30 microns or so, the thickness of the top coat may be up to about 30 microns. Average particle sizes of slightly less than the thickness of the top coat is possible since the distribution of particles will still provide a good number of particles in excess of the coating thickness and the coating thickness itself varies across the surface of the substrate to which it is applied. Thus, the goal is to ensure that an adequate number of particles have not skinned over so that a sufficient level of antimicrobial metal ion release is capable without having to wear away or remove the skin. In this respect one would want for at about least 30%, preferably at least about 40%, of the antimicrobial particles to have a diameter of equal to or less than the thickness of the coating. Though one could add greater quantities of antimicrobial agents whose average particle size is more than a micron or so less than the thickness of the coating, such would not be economical, especially in relatively low cost applications.

Where the top coat is a non-skin forming top coat, as discussed previously, the thickness of the top coat may be greater than the diameter of the particles of the antimicrobial agent provided that the particles do not settle in the coating formulation once applied. Settling has the same effect as skinning as the coating material flows over the top of the particles as they settle in the composition. The skinning effect, as mentioned herein, entails two circumstances. The first is where the particle is suspended in the coating and the coating forms a film over the surface of the particle even though the particle is at or proximate to the surface of the top coat. The second is where the coating is such that even where the antimicrobial particles protrude above the surface of the coating matrix (as for example where the particles have a greater diameter than the thickness of the coating), the surface tension forces of the coating are such that it still forms a film over the particles.

The two-layer coating can be applied to any of several surfaces. Dependent upon the surface to be coated, the base coat should be chosen to supply sufficient adhesion and wetting of the surface. These parameters are known in the art and supplied by manufacturers of various base coats. The surface can be of several compositions such as metal, plastic and wood. Surfaces that are particularly useful for coatings of this invention are ones in a highly erosive environment such as floors, mats, containers, cutting boards, shelving, conveyer belts, appliances and the like. Examples of appliance surfaces include dishwasher walls, icemakers, refrigerator shelves, showerhead faucets and the like. Other surfaces include chemical storage tanks, animal feed tanks, cooling water systems and pipes. In particular, the coating systems of the present invention are especially suited for use in food preparation and processing facilities, pharmaceutical and biotechnology related manufacturing, testing and processing facilities, and in transport vehicles and storage facilities/apparatus associated therewith including, for example, the inner walls of grain silos, rail cars, tanker trucks, bulk storage containers, etc.

The following examples are merely illustrative of the invention and are not to be deemed limiting thereof. Those skilled in the art will recognize many variations that are within the spirit of the invention and scope of the claims.

EXAMPLE 1

A base coat coating composition was prepared from a two-part cycloaliphatic amine epoxy coating system from Carboline Company, St. Louis, Mo. (Carboline 892) using 74 parts Part A (cycloaliphatic amine) and 100 parts Part B (epoxy resin). To 500 g of the 70% solids mixed base coat composition was added 12 g of a microencapsulated silver zeolite composition. The microencapsulated silver zeolite composition was prepared by microencapsulating 100 parts AgION AJ10D antimicrobial agent (about 2.5% by weight of silver ion-exchanged in Type A zeolite particles having a mean average diameter of about 3μ available from AgION Technologies, Inc., Wakefield, Mass.) with 100 parts of a hydrophilic polyurethane resin (Tecophilic® 60 from Thermedics Inc. of Woburn, Mass.). That fraction of the so formed particles having a particle size of about 40-100 microns were employed in this example. The resulting base coat coating composition contained, on a percent (by weight) solids basis, approximately 3.3% microencapsulated particles, which corresponds to approximately 1.65% AgION antimicrobial powder in the final base coat.

The above-formulated base coat composition was applied to 100 mm by 100 mm Taber abrasion test pieces of galvanized steel sheet using a compressed air spray gun. The coated test pieces were allowed to cure overnight. The thickness of the cured coating was measured with a coating thickness gage using the eddy current method. Measurements were taken at eight locations around the circumference at the wear test radius of the test pieces. The average thickness of the base coat was 160 microns.

A hydrophilic top coat coating composition was prepared from a two-part, crosslinked, waterborne, hydrophilic acrylic coating system (having a moisture absorption of about 35%; available from Surface Solutions Laboratories and described in U.S. Pat. No. 6,238,799). To 80 parts (based on the solids content) of the mixed top coat composition was added 20 parts of AgION AJ10D powder. The antimicrobial acrylic top coat was applied to the epoxy base coat using an air spray gun. After an overnight cure, the total coating thickness was measured at the same eight locations. The top coat thickness was determined by subtracting base coat measurements from the corresponding total thickness measurement at each point. The average thickness of the top coat was 26 microns.

Each coated test piece was then subjected to a Taber abrasion test and the silver release in the wear path of each sample tested at various intervals. The Taber abrasion test was conducted using a 1000 g load and an HS-10 wheel. Coating thickness in the wear path, following abrasion, was measured as before. Silver release was measured by placing each test piece in 40 ml of a 0.8% $NaNO_3$ for 24 hours at room temperature and the solution tested for silver using a graphite furnace atomic absorption (GFAA) spectrophotometer. To ensure that only release from the wear path was measured, a wax coating was applied over the un-abraded surface of the test piece. The results of the abrasion and silver release testing are shown in Table 1.

TABLE 1

| Wear Cycles | 500 | 1000 | 1500 | 3000 | 5000 | 7000 |
|---|---|---|---|---|---|---|
| Microns removed | 27 | 38 | 47 | 66 | 93 | 97 |
| [$Ag^+$] ppb | 1301 | 1034 | 940 | 1054 | 649 | 841 |

Because partial debonding of the wax from the top coat surface was seen in a couple of the test pieces subjected to the 3000 wear cycles, an additional test piece was subjected to 8,000 cycles of abrasion and, following abrasion, all the coating was removed from the un-abrade areas. These areas were then covered with the epoxy coating without the antimicrobial. Silver release was then measured, as above, and found to give a release of 203 ppb, an antimicrobially effective level of release.

Figure 7:
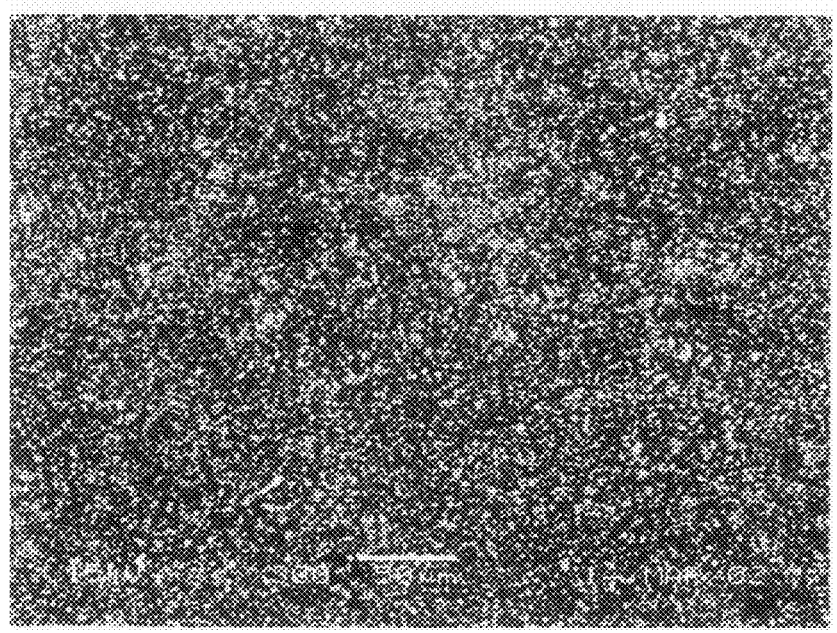
FIG. 7 is a plan view of the test piece of Example 1 treated with the erosive coating prior to abrading.
Figure 5:
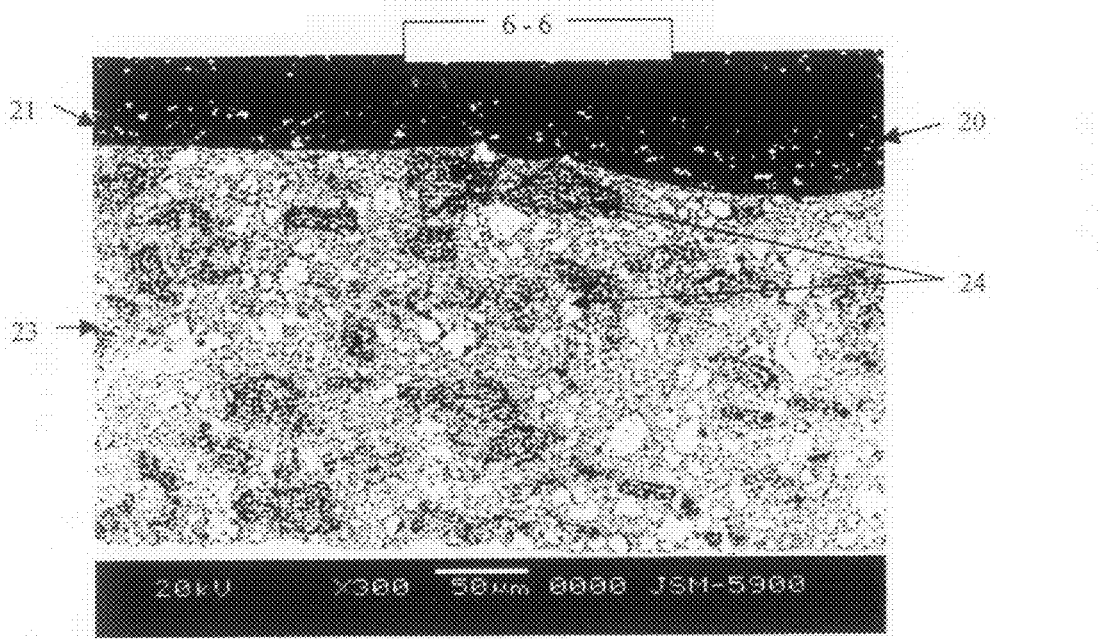
FIG. 5 is a photomicrograph of a cross-section of an erosive coating.
Figure 6:
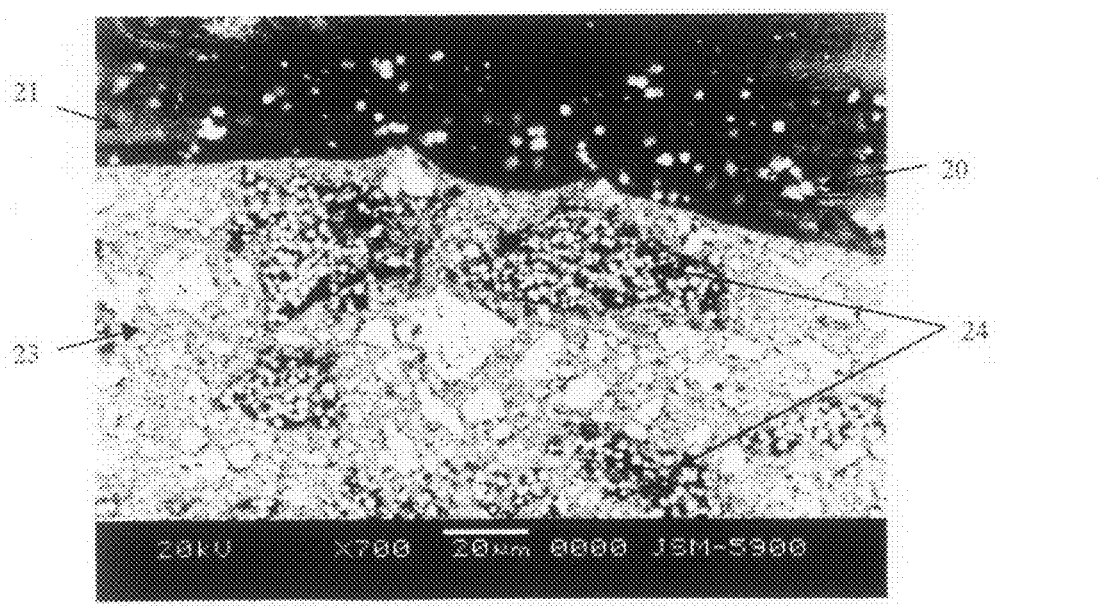
FIG. 6 is a close up of the surface of the erosive coating of FIG. 5 at point 6-6.
Figure 8:
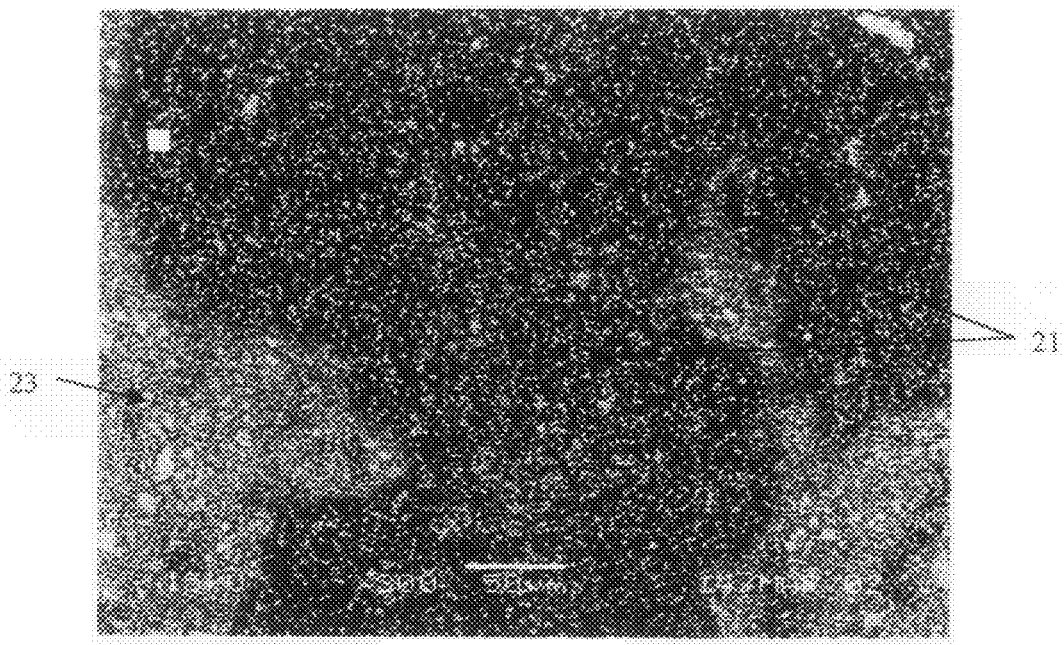
FIGS. 8 and 9 are photomicrographs of adjacent surface areas of the coated test piece shown in FIG. 7 following 500 cycle wear.
Figure 9:
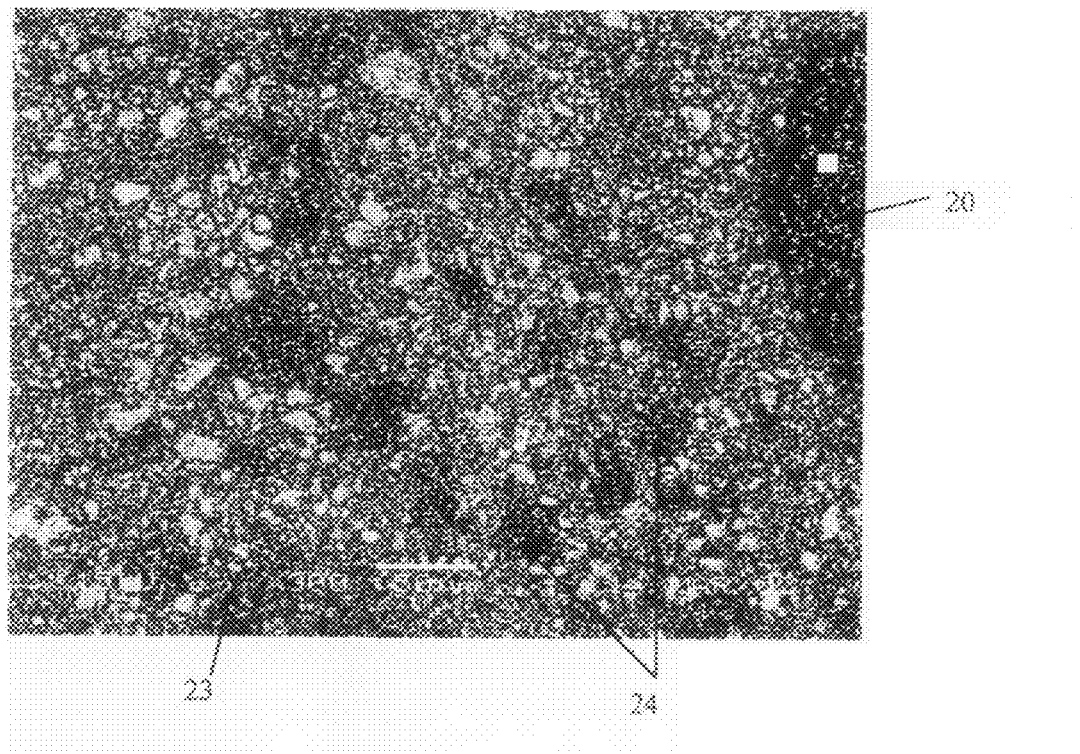

In addition to the foregoing tests, samples subjected to the 500 cycle abrasion were also characterized under Scanning Electron Microscopy. FIG. 5 shows a photomicrograph of a cross-section of a test piece in which distinct particles of the antimicrobial agent (20) are shown in acrylic top coat (21) and distinct particles of the microencapsulated antimicrobial agent (24) are shown in the base coat (23). FIG. 6 is a photomicrograph of that area depicted by the line 6-6 in FIG. 5 wherein the skinning effect (26) of the epoxy resin over the microencapsulated antimicrobial agent (24) is seen. FIG. 7 shows a plan on view of the surface of the test piece prior to abrasion. All that is seen is top coat with the therein contained particles of antimicrobial agent (lighter specs in the photo). FIGS. 8 and 9 show overlapping portions of the abraded surface following 500 cycles, with the "i" marking the key for orienting the two photomicrographs. FIG. 8 shows an area where little of the top coat (21) has been abraded away to expose the underlying base coat (23). FIG. 9, on the other hand, shows an area where most of the top coat (21) has been abraded away, exposing large areas of base coat (23) as well as particles of the microencapsulated antimicrobial agent (24).

The SEM analysis clearly showed the AgION powder in the top coat and in the microencapsulated particles in the base coat. The SEM analysis also confirms both uneven wear of the coatings and the uneven thickness and surface irregularity of each coating which accounts for the existence of exposed areas of top coat and base coat in the abraded sample and, more significantly, the variation in the silver release values. Nevertheless, even with only base coat exposure following wear, significant and efficacious silver release is attained. Perhaps the most significant revelation of the SEM analysis is that for any horizontal line through the coating, corresponding to a stage of coating erosion, the antimicrobial agent in the top coat and/or particles of microencapsulated antimicrobial agent in the base coat are intersected. The significance of consistent particle intersection with the surface is that at no time will the surface fail to have access to a source of silver as exemplified by this Example.

EXAMPLE 2

A 3-part 100% solids, trowellable epoxy flooring system (CORRO-FLOR) consisting of a resin (Part A), a Hardener (Part B) and a grit filler (blended granite or quartz aggregate) plus tint (Part C) obtained from Corro-Shield International, Inc. of Rosemont, Ill. was prepared and employed as a base coat. Prior to mixing, Part C was modified by blending the unmodified Part C with 0.2% by weight of AgION AK10D (5% by weight of silver ion-exchanged in Type A zeolite particles available from AgION Technologies, Inc., Wakefield, Mass.), based on the total weight of the coating, and a small amount of Part A to bond the antimicrobial powder to the grit for ease of incorporation. The coating was then applied to ceramic tiles using a trowel to a thickness of approximately 0.25 inch, in accordance with the manufacturer's instructions.

Several tiles prepared as set forth in the preceding paragraph were then coated with a hydrophilic acrylic top coat (Clene Coat AC from AgION Technologies, Inc. of Wakefield, Mass.) which is a 3-part coating system having 33% solids and including 5% by weight based on the total weight of the top coat coating composition of AgION AJ10D and 1% by weight, based on the total weight of the top coat coating composition, of copper-8 quinolinolate. The formulated top coat was applied over the base coat using a brush to a thickness of approximately 50 microns.

Samples of the coated tiles, with and without top coat, were then abraded using 120 grit sandpaper for about 15 seconds and with moderate pressure and scored with a knife to imitate the abuse such surfaces are likely to encounter in use. To evaluate silver release, two-inch by two-inch specimens were cut from each type of sample and the edges sealed with a silicone rubber (GE Clear Silicone) to ensure extraction from only the surface and not from the exposed edges. Each specimen was then placed in 55 ml of a 0.8% $NaNO_3$ extraction solution for 24 hours at room temperature. The extraction solutions were then analyzed using a GFAA spectrophotometer to measure the amount of silver released. The results are shown in Table 2.

TABLE 2

| Sample | Silver Release (ng) |
| --- | --- |
| Epoxy Floor Covering | 146 |
| Epoxy Floor Covering with Top coat | 751 |
| Epoxy Floor Covering with Top coat (abraded) | 505 |

As can be seen, the samples with the top coat provided far greater silver release than the sample just having the epoxy base coat. As the top coat is abraded away, exposing, in part, the underlying base coat, there is a modest drop in silver release. However, even when the top coat is fully abraded, a higher release is attained from the base coat of the two-layered coating system than with the single layer coating due to the abrasion of the skinning material concurrent with the abrasion of the top coat. While the single layer coating system would eventually show good release, as with the abraded sample, there is little release until such abrasion occurs. Accordingly, the coating system of the present invention allows for fast and high silver ion release and, thus, good antimicrobial efficacy as compared to the epoxy base coat by itself.

EXAMPLE 3

The coating system of Example 2 was applied to a real-life environment of a food processing facility. The base coat was applied to the concrete flooring in a number of high to moderate traffic areas. The concrete flooring was first prepped by blast tracking and cleaning. Parts A and B were mixed and the mix applied to the prepped floor sections by roll coating. Part C was then broadcast and back-rolled into the rolled coating, resulting in a coating of approximately 40 mil thickness. Following cure of the epoxy base coat, a 2 mil layer of the formulated acrylic top coat was rolled over the cured epoxy base coat.

Four treated and two untreated areas of the flooring having similar traffic patterns were selected for bacterial testing. Total Plate Count (TPC) and Listeria testing were performed. In determining the TPC, 2" by 2" areas were swabbed with a pre-moistened sponge swab (Spongesicle from International BioProducts) and shipped overnight to the testing facility. Upon receipt, the swab was placed in 4 ml of Butterfield's buffer and the bacteria extracted by vortexing. The fluid extracted was diluted and plated onto TSA media. The media was incubated for 48 hours at 35-37° C. and enumerated to determine the total colony forming units (cfu) per sample.

The treated and untreated surfaces were also evaluated for the presence of Listeria. Swabs were taken from 2' by 2' areas using the Listeria Isolation Swabcheck™ test kit obtained from Schleicher and Schuell MicroScience. The presence of Listeria was denoted by a color change in the test kit.

In each case, swabs were taken twice each day, pre-production and post production, for eight days. Although there was some day-to-day as well as intra-day variation in the numerical results, overall a 95% reduction in colony forming units was observed in the treated versus untreated surfaces on a pre-production basis and a 61% reduction in colony forming units was observed on a post-production basis. Similarly, the treated areas had a 41% reduction in number of positive test results for Listeria.

Although the present invention has been described with respect to the foregoing specific embodiments and examples, it should be appreciated that other embodiments utilizing the concept of the present invention are possible without departing from the scope of the invention. The present invention is defined by the claimed elements and any and all modifications, variations, or equivalents that fall within the spirit and scope of the underlying principles.

I claim:

1. A substrate which, in use, is subject to high wear or highly errosive conditions, said substrate having an antimicrobial coating which provides both immediate and long term antimicrobial bioefficacy despite the high wear or errosive conditions of use, said antimicrobial coating comprising a cured base coat coating composition and a cured top coat coating composition, each coating composition derived from a curable polymer composition containing an inorganic antimicrobial agent, wherein the cured polymer of the base coat is a non-hydrophilic material and the cured polymer of the top coat is either (a) a hydrophilic material having a water absorption at equilibrium of at least 2% by weight other than a polysaccharide or hyaluronan or (b) a non-hydrophilic material that is either (i) skin forming, provided that inorganic antimicrobial agent is in particle form and the thickness of the top coat is such that an adequate number of particles of the antimicrobial agent are not skinned over so as to preclude the presence at the surface of the top coat of an antimicrobially effective amount of the antimicrobial agent, or (ii) non skin forming with respect to the antimicrobial agent; wherein said inorganic antimicrobial agent is an antimicrobial metal or metal ion containing agent; wherein said cured non-hydrophlic base coat is thicker than and has long-term durability as compared to the top coat; and wherein the substrate is selected from the group consisting of floors, conveyer belts, appliances, chemical storage tanks, animal feed tanks, cooling water systems and pipes, storage containers, bulk storage containers, silos, and storage compartments of transport vessels, rail cars and vehicles.

2. The substrate of claim 1 wherein the substrate is selected from bulk storage containers, silos, and storage compartments of transport vessels, rail cars and vehicles.

3. The substrate of claim 1 wherein the cured top coat is a hydrophilic material.

4. The substrate of claim 3 wherein the cured hydrophilic material is selected from the group consisting of poly(alkylene ether) esters, polyacrylates, polymethacrylates, polyurethanes, polyamides, polyacrylamides, polymethacrylamides, polyvinylpyrrolidinones, polyureas, polyvinylacetates, polyvinylalcohols, copolymers of the foregoing, copolymers having a substantial presence of hydrophilic monomers used in the foregoing and blends of any two or more of the foregoing.

5. The substrate of claim 3 wherein the cured hydrophilic material is selected from the group consisting of polyhydroxyethyl methacrylate, polyacrylamide, polyurethanes, N-vinyl-2-pyrrolidinone, polylactic acid, polyamides, and blends thereof.

6. The substrate of claim 3 wherein the cured hydrophilic top coat is a polymer with water absorption at equilibrium of at least about 5% by weight.

7. The substrate of claim 3 wherein the cured hydrophilic top coat is a polymer with water absorption at equilibrium of at least about 20% by weight.

8. The substrate of claim 1 wherein the cured top coat is non-skin forming, non-hydrophilic material.

9. The substrate of claim 1 wherein the cured top coat is a skin forming non-hydrophilic material provided that the inorganic antimicrobial agent is in particle form and at least about 40% of the antimicrobial particles have a diameter that is equal to or greater than the thickness of the top coat.

10. The substrate of claim 1 wherein the cured top coat is a skin forming non-hydrophilic material provided that average diameter of the antimicrobial agent particles is about the same as or greater than the thickness of the top coat.

11. The substrate of claim 1 wherein the cured polymer of the base coat is a cured thermoset polymer and wherein antimicrobial agent entombed within the base coat is ineffective in providing antimicrobial bioefficacy at the coating surface.

12. The substrate of claim 11 wherein the thermoset polymer is chosen from the group consisting of phenolic resins, urea resins, epoxy resins, polyesters, epoxy polyesters, acrylics, and polyurethanes.

13. The substrate of claim 12 wherein the thermoset polymer is an epoxy resin.

14. The substrate of claim 1 wherein the inorganic antimicrobial agent comprises a metal or metal ion selected from silver, copper, zinc, tin, gold, mercury, lead, iron, cobalt, nickel, manganese, arsenic, antimony, bismuth, barium, cadmium, chromium and thallium ions and combinations thereof.

15. The substrate of claim 14 wherein the metal or metal ion is silver, zinc, copper or a combination of any two or all three of the foregoing.

16. The substrate of claim 14 wherein each of the antimicrobial agents is independently selected from the group consisting of metal salts, antimicrobial metal or metal ion containing water soluble glasses, antimicrobial metal ion-exchange type antimicrobial agents and combinations thereof.

17. The substrate of claim 16 wherein the antimicrobial agent is an ion-exchange type antimicrobial agent comprising a ceramic carrier and ion-exchanged antimicrobial metal ions.

18. The substrate of claim 17 wherein the ceramic carrier is selected from the group consisting of zeolites, hydroxyapatites, and zirconium phosphates.

19. The substrate of claim 16 wherein both of the antimicrobial agents are ion-exchange type antimicrobial agents.

20. The substrate of claim 16 wherein at least one of the antimicrobial agents is encapsulated in a hydrophilic polymer.

21. The substrate of claim 20 wherein the antimicrobial agent in the base coat is an encapsulated ion-exchange type antimicrobial agent comprising a ceramic carrier having ion-exchanged antimicrobial metal ions.

22. The substrate of claim 20 wherein each particle of the encapsulated antimicrobial agent includes a plurality of particles of the antimicrobial agent.

23. The treated substrate of claim 1 wherein the substrate is a floor in a food preparation and processing facility or in a pharmaceutical or biotechnology related manufacturing, testing or processing facility.

* * * * *